United States Patent
Hansen et al.

(10) Patent No.: US 8,114,995 B2
(45) Date of Patent: Feb. 14, 2012

(54) METHODS OF PREPARING QUINAZOLINONE DERIVATIVES

(75) Inventors: Henrik C. Hansen, Calgary (CA); Shubham P. Chopade, Florence, SC (US); Janakiram R. Citineni, Florence, SC (US); Robert P. Short, Florence, SC (US); George P. Yiannikouros, Florence, SC (US)

(73) Assignee: Resverlogix Corp., Calgary, AB (CA)

( * ) Notice: Subject to any disclaimer, the term of this patent is extended or adjusted under 35 U.S.C. 154(b) by 302 days.

(21) Appl. No.: 12/490,877

(22) Filed: Jun. 24, 2009

(65) Prior Publication Data
US 2010/0004448 A1  Jan. 7, 2010

Related U.S. Application Data

(60) Provisional application No. 61/075,952, filed on Jun. 26, 2008.

(51) Int. Cl.
C07D 239/91  (2006.01)
(52) U.S. Cl. .................................................. 544/289
(58) Field of Classification Search .................. 544/289
See application file for complete search history.

(56) References Cited

U.S. PATENT DOCUMENTS

| | | |
|---|---|---|
| 2,065,593 A | 12/1936 | Lubs |
| 2,065,900 A | 12/1936 | Laska et al. |
| 2,071,329 A | 2/1937 | Brown |
| 3,251,837 A | 5/1966 | Holland |
| 3,600,394 A | 8/1971 | Coyne et al. |
| 3,773,946 A | 11/1973 | Creger |
| 3,930,024 A | 12/1975 | Creger |
| 3,965,128 A | 6/1976 | Fürst et al. |
| 4,613,593 A | 9/1986 | Yamatsu et al. |
| 4,689,344 A | 8/1987 | Bar-Tana |
| 4,711,896 A | 12/1987 | Bar-Tana et al. |
| 4,825,005 A | 4/1989 | Frey et al. |
| 5,124,337 A | 6/1992 | Dugar et al. |
| 5,126,351 A | 6/1992 | Luzzio |
| 5,244,904 A | 9/1993 | Nagase et al. |
| 5,280,024 A | 1/1994 | Bolland et al. |
| 5,354,749 A | 10/1994 | Dressel et al. |
| 5,407,942 A | 4/1995 | Dressel et al. |
| 5,446,071 A | 8/1995 | Grese |
| 5,480,883 A | 1/1996 | Spada et al. |
| 5,539,119 A | 7/1996 | Nagase et al. |
| 5,576,322 A | 11/1996 | Takase et al. |
| 5,595,974 A | 1/1997 | Tomaru |
| 5,693,652 A | 12/1997 | Takase et al. |
| 5,707,987 A | 1/1998 | Nakagawa et al. |
| 5,733,913 A | 3/1998 | Blankley et al. |
| 5,756,344 A | 5/1998 | Onda et al. |
| 5,756,544 A | 5/1998 | Bisgaier et al. |
| 5,756,736 A | 5/1998 | Arzeno et al. |
| 5,756,763 A | 5/1998 | Takeuchi et al. |
| 5,763,414 A | 6/1998 | Bok et al. |
| 5,783,577 A | 7/1998 | Houghten et al. |
| 5,792,461 A | 8/1998 | Bok et al. |
| 5,792,902 A | 8/1998 | Benoit et al. |
| 5,798,344 A | 8/1998 | Kuroki et al. |
| 5,801,180 A | 9/1998 | Takase et al. |
| 5,817,674 A | 10/1998 | Clemence et al. |
| 5,854,264 A | 12/1998 | Anthony et al. |
| 5,877,208 A | 3/1999 | Bok et al. |
| 5,922,866 A | 7/1999 | Miyata et al. |
| 5,965,556 A | 10/1999 | Takeuchi et al. |
| 6,022,901 A | 2/2000 | Goodman |
| 6,048,903 A | 4/2000 | Toppo |
| 6,054,435 A | 4/2000 | Or et al. |
| 6,133,241 A | 10/2000 | Bok et al. |
| 6,165,984 A | 12/2000 | Bok et al. |
| 6,168,776 B1 | 1/2001 | Klunk et al. |
| 6,239,114 B1 | 5/2001 | Guthrie |
| 6,291,456 B1 | 9/2001 | Stein et al. |
| 6,303,629 B1 | 10/2001 | Kun |
| 6,340,759 B1 | 1/2002 | Ueno et al. |

(Continued)

FOREIGN PATENT DOCUMENTS

AU   719140   7/1998

(Continued)

OTHER PUBLICATIONS

Abdel-Jalil et al., "Synthesis and Antitumor Activity of 2-Aryl-7-fluoro-6-(4-methyl-1-piperazinyl)-4(3H)-quinazolinones" *Heterocycles* 65(9):2061-2070 (2005).

Abdul-Rahman, A. et al., "Dinuclear molybdenum complexes derived from diphenols: electrochemical interactions and reduced species" *Polyhedron* 16(24):4353-4362 (1997).

Acton, S. et al., "Identification of Scavenger Receptor SR-BI as a High Density Lipoprotein Receptor" *Science* 271:518-520 (1996).

(Continued)

*Primary Examiner* — James O Wilson
*Assistant Examiner* — Brian McDowell
(74) *Attorney, Agent, or Firm* — Finnegan, Henderson, Farabow, Garrett, & Dunner LLP

(57) ABSTRACT

The present disclosure relates to methods for preparing compounds, which are useful for regulating the expression of apolipoprotein A-I (ApoA-I), and in the treatment and prevention of cardiovascular disease and related disease states, including cholesterol- or lipid-related disorders, such as, for example, atherosclerosis.

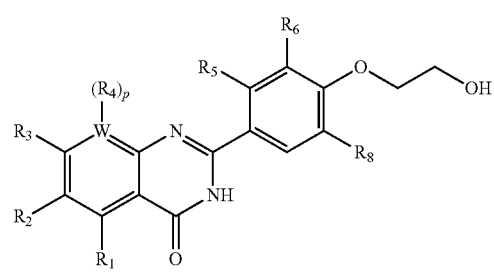

7 Claims, No Drawings

U.S. PATENT DOCUMENTS

| | | |
|---|---|---|
| 6,414,037 B1 | 7/2002 | Pezzuto et al. |
| 6,455,577 B2 | 9/2002 | Bok et al. |
| 6,482,479 B1 | 11/2002 | Dübal et al. |
| 6,512,161 B1 | 1/2003 | Rouy et al. |
| 6,541,045 B1 | 4/2003 | Charters et al. |
| 6,541,522 B2 | 4/2003 | Inman et al. |
| 6,548,548 B2 | 4/2003 | Campbell et al. |
| 6,613,772 B1 | 9/2003 | Schindler et al. |
| 6,635,642 B1 | 10/2003 | Jackson et al. |
| 6,673,780 B2 | 1/2004 | Dasseux et al. |
| 6,703,422 B2 | 3/2004 | Dasseux et al. |
| 7,087,612 B2 | 8/2006 | Rodriguez Sarmiento et al. |
| 7,173,128 B2 | 2/2007 | Ravichandran et al. |
| 7,244,776 B2 | 7/2007 | Ravichandran et al. |
| 2002/0004608 A1 | 1/2002 | Alig et al. |
| 2002/0091263 A1 | 7/2002 | Trova |
| 2003/0064967 A1 | 4/2003 | Luchoomun et al. |
| 2003/0068526 A1 | 4/2003 | Kamatani et al. |
| 2003/0072964 A1 | 4/2003 | Kwong et al. |
| 2003/0171429 A1 | 9/2003 | Chen et al. |
| 2004/0001834 A1 | 1/2004 | Kim et al. |
| 2004/0033480 A1 | 2/2004 | Wong |
| 2004/0058903 A1 | 3/2004 | Takasugi et al. |
| 2004/0097493 A1 | 5/2004 | Chen et al. |
| 2004/0147788 A1 | 7/2004 | Savouret et al. |
| 2004/0198750 A1 | 10/2004 | Green et al. |
| 2004/0235877 A1 | 11/2004 | Ishizuka et al. |
| 2004/0235888 A1 | 11/2004 | Yamamori et al. |
| 2004/0242615 A1 | 12/2004 | Yamamori et al. |
| 2004/0248950 A1 | 12/2004 | Ishizuka et al. |
| 2005/0043300 A1 | 2/2005 | Middleton et al. |
| 2005/0080021 A1 | 4/2005 | Tucker et al. |
| 2005/0080024 A1 | 4/2005 | Tucker et al. |
| 2005/0261319 A1 | 11/2005 | Deuschle et al. |
| 2006/0116364 A1 | 6/2006 | Hamaoka et al. |
| 2006/0205767 A1 | 9/2006 | Wong et al. |
| 2006/0205792 A1 | 9/2006 | Wong et al. |
| 2007/0185160 A1 | 8/2007 | Hattori et al. |
| 2007/0218155 A1 | 9/2007 | Kuhrts |
| 2008/0188467 A1 | 8/2008 | Wong et al. |
| 2008/0275069 A1 | 11/2008 | Mizutani et al. |
| 2009/0029987 A1 | 1/2009 | Wong et al. |
| 2009/0259048 A1 | 10/2009 | Wong et al. |
| 2011/0082176 A1 | 4/2011 | Wong et al. |

FOREIGN PATENT DOCUMENTS

| | | |
|---|---|---|
| CA | 2104981 A1 | 3/1994 |
| CA | 2345406 A1 | 4/2000 |
| CN | 1067070 C | 6/2001 |
| DE | 637259 | 10/1936 |
| DE | 652772 | 11/1937 |
| DE | 36 01 417 A1 | 7/1987 |
| DE | 42 15 588 A1 | 11/1993 |
| DE | 196 51 099 A1 | 6/1998 |
| DE | 197 56 388 A1 | 6/1999 |
| DE | 199 34 799 A1 | 2/2001 |
| EP | 0 210 342 A2 | 2/1987 |
| EP | 0 258 190 B1 | 3/1988 |
| EP | 0 182 213 B1 | 9/1990 |
| EP | 0 407 217 A1 | 1/1991 |
| EP | 0 488 602 A1 | 6/1992 |
| EP | 0 272 455 B1 | 2/1993 |
| EP | 0 564 350 B1 | 10/1993 |
| EP | 0 375 404 B1 | 2/1994 |
| EP | 0 333 175 B1 | 6/1994 |
| EP | 0 343 499 B1 | 7/1994 |
| EP | 0 409 413 B1 | 8/1994 |
| EP | 0 420 511 B1 | 8/1994 |
| EP | 0 633 022 A2 | 1/1995 |
| EP | 0 569 795 B1 | 4/1995 |
| EP | 0 330 108 B1 | 12/1995 |
| EP | 0 747 051 A2 | 12/1996 |
| EP | 0 643 119 B1 | 4/2000 |
| EP | 1 125 908 A1 | 8/2001 |
| EP | 0 498 723 B1 | 9/2001 |
| EP | 0 607 439 B1 | 1/2002 |
| EP | 0 776 893 B1 | 2/2002 |
| EP | 1 195 378 A1 | 4/2002 |
| EP | 1 277 738 A1 | 1/2003 |
| EP | 1 398 032 A1 | 3/2004 |
| EP | 1 418 164 A1 | 5/2004 |
| EP | 1 426 046 A1 | 6/2004 |
| EP | 1 477 481 A1 | 11/2004 |
| EP | 1 637 523 A1 | 3/2006 |
| EP | 2 005 941 A2 | 12/2008 |
| FR | 803201 | 9/1936 |
| FR | 803619 | 10/1936 |
| FR | 2244492 | 4/1975 |
| FR | 2244493 | 4/1975 |
| GB | 472489 | 9/1937 |
| GB | 728767 | 4/1955 |
| GB | 1175808 | 12/1969 |
| GB | 1179019 | 1/1970 |
| GB | 2 292 149 A | 2/1996 |
| JP | 6-80656 A | 3/1994 |
| JP | 7-041442 A | 2/1995 |
| JP | 7-061942 A | 3/1995 |
| JP | 7-118241 A | 5/1995 |
| JP | 7-179380 A | 7/1995 |
| JP | 7-233109 A | 9/1995 |
| JP | 7-247289 A | 9/1995 |
| JP | 10-287678 A | 10/1998 |
| JP | 2001-131151 A | 5/2001 |
| JP | 2001-139550 A | 5/2001 |
| JP | 2001-335476 A | 12/2001 |
| JP | 2002-249483 A | 9/2002 |
| JP | 2004-203751 A | 7/2004 |
| JP | 2004-307440 A | 11/2004 |
| KR | 10-0707532 B1 | 4/2007 |
| WO | WO 91/18901 A1 | 12/1991 |
| WO | WO 92/09374 A1 | 6/1992 |
| WO | WO 92/18123 A2 | 10/1992 |
| WO | WO 92/20642 A1 | 11/1992 |
| WO | WO 92/21661 A1 | 12/1992 |
| WO | WO 93/07124 A1 | 4/1993 |
| WO | WO 93/08174 A1 | 4/1993 |
| WO | WO 94/14763 A1 | 7/1994 |
| WO | WO 95/03277 A1 | 2/1995 |
| WO | WO 95/23150 A1 | 8/1995 |
| WO | WO 96/15128 A1 | 5/1996 |
| WO | WO 96/31206 A2 | 10/1996 |
| WO | WO 97/10221 A1 | 3/1997 |
| WO | WO 97/15308 A1 | 5/1997 |
| WO | WO 97/28118 A1 | 8/1997 |
| WO | WO 97/28132 A1 | 8/1997 |
| WO | WO 97/28134 A1 | 8/1997 |
| WO | WO 97/29106 A1 | 8/1997 |
| WO | WO 97/48694 A1 | 12/1997 |
| WO | WO 98/11438 A1 | 3/1998 |
| WO | WO 98/26127 A1 | 6/1998 |
| WO | WO 98/30530 A1 | 7/1998 |
| WO | WO 98/50370 A1 | 11/1998 |
| WO | WO 98/51307 A1 | 11/1998 |
| WO | WO 98/51308 A1 | 11/1998 |
| WO | WO 98/55124 A1 | 12/1998 |
| WO | WO 99/00116 A2 | 1/1999 |
| WO | WO 99/11634 A1 | 3/1999 |
| WO | WO 99/18077 A1 | 4/1999 |
| WO | WO 99/29667 A1 | 6/1999 |
| WO | WO 00/17184 A1 | 3/2000 |
| WO | WO 00/23075 A1 | 4/2000 |
| WO | WO 00/35865 A2 | 6/2000 |
| WO | WO 00/44362 A2 | 8/2000 |
| WO | WO 00/55168 A1 | 9/2000 |
| WO | WO 00/64888 A1 | 11/2000 |
| WO | WO 01/00554 A2 | 1/2001 |
| WO | WO 01/60775 A1 | 8/2001 |
| WO | WO 01/82916 A2 | 11/2001 |
| WO | WO 01/83456 A1 | 11/2001 |
| WO | WO 02/44189 A1 | 6/2002 |
| WO | WO 02/074307 A1 | 9/2002 |
| WO | WO 02/087556 A2 | 11/2002 |
| WO | WO 02/096426 A1 | 12/2002 |
| WO | WO 03/007959 A1 | 1/2003 |
| WO | WO 03/016292 A1 | 2/2003 |
| WO | WO 03/018008 A1 | 3/2003 |

| | | |
|---|---|---|
| WO | WO 03/040256 A2 | 5/2003 |
| WO | WO 03/040257 A1 | 5/2003 |
| WO | WO 03/070236 A2 | 8/2003 |
| WO | WO 03/099274 A1 | 12/2003 |
| WO | WO 03/106435 A1 | 12/2003 |
| WO | WO 2004/017920 A2 | 3/2004 |
| WO | WO 2004/032846 A2 | 4/2004 |
| WO | WO 2004/037176 A2 | 5/2004 |
| WO | WO 2004/039795 A2 | 5/2004 |
| WO | WO 2004/047755 A2 | 6/2004 |
| WO | WO 2004/056355 A1 | 7/2004 |
| WO | WO 2004/058717 A1 | 7/2004 |
| WO | WO 2004/065392 A1 | 8/2004 |
| WO | WO 2004/072042 A2 | 8/2004 |
| WO | WO 2004/092196 A2 | 10/2004 |
| WO | WO 2004/094452 A2 | 11/2004 |
| WO | WO 2004/112710 A2 | 12/2004 |
| WO | WO 2005/034960 A1 | 4/2005 |
| WO | WO 2005/065183 A2 | 7/2005 |
| WO | WO 2005/066162 A1 | 7/2005 |
| WO | WO 2005/075431 A1 | 8/2005 |
| WO | WO 2005/115993 A1 | 12/2005 |
| WO | WO 2006/012577 A2 | 2/2006 |
| WO | WO 2006/045010 A2 | 4/2006 |
| WO | WO 2006/045096 A2 | 4/2006 |
| WO | WO 2006/071095 A1 | 7/2006 |
| WO | WO 2006/105081 A2 | 10/2006 |
| WO | WO 2007/016525 A2 | 2/2007 |
| WO | WO 2007/071055 A1 | 6/2007 |
| WO | WO 2008/092231 A1 | 8/2008 |
| WO | WO 2010/079431 A2 | 7/2010 |

OTHER PUBLICATIONS

Asztalos, "High-Density Lipoprotein Metabolism and Progression of Atherosclerosis: New Insights from the HDL Atherosclerosis Treatment Study" *Curr. Opin. Cardiol.* 19:385-391 (2004).
Baba et al., "Continuous intake of polyphenolic compounds containing cocoa powder reduces LDL oxidative susceptibility and has beneficial effects on plasma HDL-cholesterol concentrations in humans" *Am. J. Clin. Nutr.* 85:709-717 (2007).
Badimon et al., "Role of High Density Lipoproteins in the Regression of Atherosclerosis" *Circulation* 86(Suppl. III):86-94 (1992).
Barrans et al., "Pre-β HDL: Structure and Metabolism" *Biochim. Biophys. Acta* 1300:73-85 (1996).
Barter et al., "High Density Lipoproteins and Coronary Heart Disease" *Atherosclerosis* 121:1-12 (1996).
Barter et al., "Antiinflammatory Properties of HDL" *Circ. Res.* 95:764-772 (2004).
Bayly, S.R. et al., "Electronic and magnetic metal-metal interactions in dinuclear oxomolybdenum(V) complexes across bis-phenolate bridging ligands with different spacers between the phenolate termini: ligand-centered vs. metal-centered redox activity" *J. Chem. Soc., Dalton Transactions* 9:1401-1414 (2001).
Bertele et al., "Platelet Thromboxane Synthetase Inhibitors with Low Doses of Aspirin: Possible Resolution of the 'Aspirin Dilemma'" *Science* 220:517-519 (1983).
Beugelmans et al., "One-pot Synthesis of 1-Oxo-1,2-Dihydroisoquinolines (Isocarbostyrils) Via SRN1 (Ar) Reactions" *Synthesis* 9:729-731 (1981).
Bhilare, S.V. et al., "Ionic-Liquid-Influenced Expeditious and Stereoselective Synthesis of Olefins" *Synthetic Communications* 37(18):3111-3117 (2007).
Bisagni et al., "A Convenient Way to Dibenzo[c,h]-1,5-Naphthyridines (11-Aza-Benzo[c]phenanthridines)" *Tetrahedron* 52:10427-10440 (1996).
Bisgaier et al., "A Novel Compound that Elevates High Density Lipoprotein and Activates the Peroxisome Proliferator Activated Receptor" *J. Lipid Res.* 39:17-30 (1998).
Boyce et al., "The Acylation and Alkylation of o-Toluinitrile. A New Route to 3-Substituted Isocarbostyrils" *J. Org. Chem.* 31:3807-3809 (1966).
Bradsher et al., "A New Isoquinoline Synthesis Via ORTHO-Substituted Benzylamines" *Tetrahedron Lett.* 31:3149-3150 (1972).
Bradsher et al., "α-Acyl-o-Toluinitriles As Intermediates in the Preparation of 3-Substituted Isoquinolines and 1-Amino-2-Benzopyrylium Derivatives" *J. Org. Chem.* 43:3817-3820 (1978).
Buhle, E.L. et al.,"Trivalent carbon. II. Unsymmetrical Hexaaryldimethyl peroxides" *J. Am. Chem. Soc.* 65:584-586 (1943).
Caplus Accession No. 2005:46491, Qin et al., "Synthesis and fungicidal activity of 5,7-dihydroxyldiazinflavanones" [online]. Retrieved from STN on Jan. 31, 2011. Also published in: *Huazhong Shifan Daxue Xuebao Zirankexueban* 38(3):323-325 (2004).
Caplus Accession No. 2004:11346, Hu et al., "Synthesis and fungicidal activity of flavanone derivatives containing isopentenyl group" [online]. Retrieved from STN on Jan. 31, 2011. Also published in: *Yingyong Huaxue* 20(12):1161-1165 (2003).
Caplus Accession No. 2003:554477, Qin et al., "Synthesis and fungicidal activity of novel diazaflavanones" [online]. Retrieved from STN on Jan. 31, 2011. Also published in: *Nongyaoxue Xuebao* 4(4):28-32 (2002).
Caplus Accession No. 1991:449453, Liu et al. "Synthesis of 2-aryl-9-bromo-4-oxo-4H-pyrano[3,2-c] quinolines" [online]. Retrieved from STN on Jan. 31, 2011. Also published in: *Youji Huaxue* 11(2):191-195 (1991).
Chakrabarty et al., "Induction of apoptosis in human cancer cell lines by diospyrin, a plant-derived bisnaphthoquinonoid, and its synthetic derivatives" *Cancer Letters* 188(1-2):85-93 (2002).
Cherubini et al., "Role of antioxidants in Atherosclerosis: Epidemiological and Clinical Update" *Curr. Pharm. Des.* 11:2017-2032 (2005).
Cho et al., "Molecular Modeling of 3-Arylisoquinoline Antitumor Agents Active Against A-549. A Comparative Molecular Field Analysis Study" *Bioorg. Med. Chem.* 10:2953-2961 (2002).
Cho et al., "Synthesis and Biological Evaluation of 3-Arylisoquinolines As Antitumor Agents" *Bioorg. Med. Chem. Lett.* 8:41-46 (1998).
Cho et al., "Synthesis and Antitumor Activity of 3-Arylisoquinoline Derivatives" *Arch. Pharm. Res.* 20:264-268 (1997).
Cho et al., "Synthesis and Comparative Molecular Field Analysis (CoMFA) of Antitumor 3-Arylisoquinoline Derivatives" *Bioorg. Med. Chem.* 6(12):2449-2458 (1998).
Chyu et al., "Differential Effects of Green Tea-Derived Catechin on Developing Versus Established Atherosclerosis in Apolipoprotein E-Null Mice" *Circulation* 109:2448-2453 (2004).
Clarkson et al., "Inhibition of Postmenopausal Atherosclerosis Progression: A Comparison of the Effects of Conjugated Equine Estrogens and Soy Phytoestrogens" *J. Clin. Endoctinol. Metab.* 86(1):41-47 (2001).
Clauson-Kaas et al., "Reactions of 3,4-dihydor-2H-pyrrido[3,2-b]-1,4-oxazines" *Acta Chemica Scandinavica* 25(8):3135-3143 (1971). Retrieved from STN, file HCAPLUS, Accession No. 1972:34186 (Abstract).
Connolly et al., "Synthesis of quinazolinones and quinazolines" *Tetrahedron* 61(43):10153-10202 (2005).
Cooper et al., "Wine polyphenols and promotion of cardiac health" *Nutr. Res. Rev.* 17:111-129 (2004).
Cramer et al., "New Syntheses of Aryl Fluorides and Aryl Fluorosulfonates from Oxyflourides of Sulfur" *J. Org. Chem.* 26:4164-4165 (1961).
Dai et al., "Synthesis of 3,4-disubstituted Isoquinolines Via Palladium-Catalyzed Cross-Coupling of 2-(1-alkynyl)benzaldimines and Organic Halides" *J. Org. Chem.* 68:920-928 (2003).
Dai et al., "Synthesis of 3-Substituted 4-Aroylisoquinolines via Pd-Catalyzed Carbonylative Cyclization of 2-(1-Alkynyl)benzaldimines" *J. Org. Chem.* 67:7042-7047 (2002).
Dansky et al., "High-Density Lipoprotein and Plaque Regression the Good Cholesterol Gets Even Better" *Circulation* 100:1762-1763 (1999).
Decossin et al., "Subclasses of LpA-I in Coronary Artery Disease: Distribution and Cholesterol Efflux Ability" *Eur. J. Clin. Invest.* 27:299-307 (1997).
Eiden, F. et al.,"1,2-Bisbenzopyranyl-ethene" *Archiv. der Pharmazie* 313(2):120-128 (1980) (German).
Esterbauer et al., "Continuous Monitoring of in Vitro Oxidation of Human Low Density Lipoprotein" *Free Radical Res. Commun.* 6:67-75 (1989).
Ferreira et al., "Diversity of Structure and Function in Oligomeric Flavanoids" *Tetrahedron* 48:1743-1803 (1992).

Fielding et al., "Molecular Physiology of Reverse Cholesterol Transport" *J. Lipid Res.* 36:211-228 (1995).

Fieser, L.F., "The potentials of some unstable oxidation-reduction systems" *J. Am. Chem. Soc.* 52:4915-4940 (1930).

Fisher Center for Alzheimer'S Research Foundation, "Alzheimer's Disease: 'Good' Cholesterol May Help Keep Alzheimer's at Bay" The Ninth International Conference on Alzheimer's Disease and Related Disorders, Philadelphia, PA, Jul. 22, 2004. Retrieved from the Internet: http://www.alzinfo.org/newsarticle/templates/archivenewstemplate.asp?articleid=156&zoneid=7 on Jul. 28, 2010 (3 pages).

Flammang et al., "2,3-Benzodiazepines: 2-Aminoisoquinolinones From Ring Contraction of 1-oxo-2,3-Benzodiazepines" *C R Acad. Sci. Paris, Series C* 290:361-363 (1980) (French).

Fokialakis et al., "A New Class of Phytoestrogens: Evaluation of the Estrogenic Activity of Deoxybenzoins" *Chem. Biol.* 11:397-406 (2004).

Gaziano et al., "Relation Between Systemic Hypertension and Blood Lipids on the Risk of Myocardial Infarction" *Am. J. Cardiol.* 84(7):768-773 (1999).

Gerritsen et al., "Flavenoids inhibit cytokine-induced endothelial cell adhesion protein gene expression" *Am. J. Pathol.* 147(2):278-292 (1995).

Gidez et al., "Separation and Quantitation of Subclasses of Human Plasma High Density Lipoproteins by a Simple Precipitation Procedure" *J. Lipid Res.* 23:1206-1223 (1982).

Gordon et al., "High Density Lipoprotein As a Protective Factor Against Coronary Heart Disease" *Am. J. Med.* 62(5):707-714 (1977).

Grundy et al., "Definition of Metabolic Syndrome" *Circulation* 109:433-438 (2004).

Gugler et al., "Disposition of Quercetin in Man After Single Oral and Intravenous Doses" *Eur. J. Clin. Pharmacol.* 9:229-234 (1975).

Guillory, J.K., "Generation of Polymorphs, Hydrates, Solvates, and Amorphous Solids" Brittain, Harry G. (ed.) *Polymorphism in Pharmaceutical Solids*, vol. 95. Marcel Dekker, Inc., New York; pp. 202-208 (1999).

Hakamata et al., "Differential effects of an acyl-coenzyme A: cholesterol acyltransferase inhibitor on HDL-induced cholesterol efflux from rat macrophage foam cells" *FEBS Letters* 363:29-32 (1995).

Haneke, "*trans*-Resveratrol, [501-36-0], Review of Toxicological Literature" Nat. Inst. Environ. Health Sciences Contract No. NO1-ES-65402 Mar. 2002.

Hazra et al., "New diospyrin derivatives with improved tumour inhibitory activity towards Ehrlich ascites carcinoma" *Medical Science Research* 22(5):351-353 (1994).

Hazra et al., "Synthesis of an antitumor derivative of diospyrin" *IRCS Medical Science* 14(1):35-36 (1986).

Heeg et al., "Plasma Levels of Probucol in Man After Single and Repeated Oral Doses" *La Nouvelle Presse Medicale* 9:2990-2994 (1980), Abstract.

Hemingway, R.W. et al.,"Gas-liquid chromatographic examination of stilbene derivatives" *J. Chromatography* 50(3):391-399 (1970).

Hertog et al., "Dietary Antioxidant Flavonoids and Risk of Coronary Heart Disease: The Zutphen Elderly Study" *Lancet* 342:1007-1011 (1993).

Hidaka et al., "Affinity Purification of the Hepatic High-Density Lipoprotein Receptor Identifies Two Acidic Glycoproteins and Enables Further Characterization of Their Binding Properties" *Biochem. J.* 284:161-167 (1992).

Hirano et al., "Genetic Cholesteryl Ester Transfer Protein Deficiency Is Extremely Frequent in the Omagari Area of Japan. Marked Hyperalphalipoproteinemia Caused by CETP Gene Mutation Is Not Associated With Longevity" *Arterioscler. Thromb. Vasc. Biol.* 17:1053-1059 (1997).

Hisano, T. et al., "Studies on organosulfur compounds. XII. Syntheses and pharmacological activities of 2-heterocyclic substituted 4(3h)-quinazolinones" *Chem. Pharm. Bull.*23(9):1910-1916 (1975).

Huang et al., "Synthesis of Isoquinolines by Palladium-Catalyzed Cyclization, Followed by a Heck Reaction" *Tetrahedron Lett.* 43:3557-3560 (2002).

International Search Report and Written Opinion issued in International Application No. PCT/CA2004/001818; Date of Mailing: Feb. 28, 2005.

International Search Report and Written Opinion issued in International Application No. PCT/CA2007/000146; Date of Mailing: Oct. 29, 2007.

International Search Report and Written Opinion issued in International Application No. PCT/IB2010/000159; Date of Mailing: Aug. 5, 2010.

International Search Report and Written Opinion issued in International Application No. PCT/US2005/038048; Date of Mailing: Mar. 7, 2007.

International Search Report and Written Opinion issued in International Application No. PCT/US2006/029827; Date of Mailing: Apr. 16, 2007.

International Search Report and Written Opinion issued in International Application No. PCT/US2005/037719; Date of Mailing: Feb. 2, 2007.

International Search Report and Written Opinion issued in International Application No. PCT/US2009/048457; Date of Mailing: Oct. 16, 2009.

Ishibashi et al., "Hypercholesterolemia in Low Density Lipoprotein Receptor Knockout Mice and its Reversal by Adenovirus-Mediated Gene Delivery" *J. Clin. Invest.* 92:883-893 (1993).

Ishibashi et al., "Massive Xanthomatosis and Atherosclerosis in Cholesterol-Fed Low Density Lipoprotein Receptor-Negative Mice" *J. Clin. Invest.* 93:1885-1893 (1994).

Jayatilake et al., "Kinase Inhibitors From Polygonum Cuspidatum" *J. Nat. Prod.* 56:1805-1810 (1993).

Jensen et al., "Serum Lipids and Anthropometric Factors Related to the Prevalence of Intermittent Claudication" *Eur. J. Vasc. Endovasc. Surg.* 30:582-587 (2005).

Jeong et al., "Hypocholesterolemic activity of hesperetin derivatives" *Bioorg. Med. Chem. Lett.* 13:2663-2665 (2003).

Jin et al., "Antiplatelet and antithrombotic activities of CP201, a newly synthesized 1,4-naphthoquinone derivative" *Vasc. Pharmacol.* 41(1):35-41 (2004).

Kalusa et al., "An efficient synthesis of 2,3-diaryl (3H)-quinazolin-4-ones via imidoyl chlorides" *Tetrahedron Letters* 49(41):5840-5842 (2008).

Kawamatsu et al., "2-Amino-4-Phenylthiazole Derivatives as Anti-Atherogenic Agents" *Eur. J. Med. Chem.* 16(4):355-362 (1981).

Kilbourne et al., "Involvement of Early Growth Response Factor Egr-1 in Apolipoprotein Al Gene Transcription" *J. Biol. Chem.* 270:7004-7010 (1995).

Kim et al., "Hypothetical Drug Binding Receptor Site Analysis Using CoMFA Method for 3-Arylisoquinolines Active Against SK-OV-3 Tumor Cell Line" *Yakhak Hoechi* 46(4):219-225 (2002).

Koudinov et al., "Alzheimer's amyloid beta and lipid metabolism: a missing link?" *FASEB J.* 12:1097-1099 (1998).

Kublak et al., "The preparation of the aza-spirobicyclic system of discorhabdin c via an intramolecular phenolate alkylation" *Tetrahedron Lett.* 31(27):3845-3848 (1990).

Kulkarni, K.R. et al.,"Quantification of HDL2 and HDL3 Cholesterol by the Vertical Auto Profile-II (VAP-II) Methodology" *J. Lipid Res.* 38:2353-2364 (1997).

Kurata et al., "A Candidate High Density Lipoprotein (HDL) Receptor, $HB_2$, With Possible Multiple Functions Shows Sequence Homology with Adhesion Molecules" *J. Atheroscler. Thromb.* 4:112-117 (1998).

Kurowska et al., "Essential Amino Acids in Relation to Hypercholesterolemia Induced in Rabbits by Dietary Casein" *J. Nutr.* 120:831-836 (1990).

Kuzuya et al., "Probucol Prevents Oxidative Injury to Endothelial Cells" *J. Lipid Res.* 32:197-204 (1991).

Laarhoven, W.H. et al., "Syntheses, infrared spectra and molecular refractions of some sterically hindered p,p'-dimethoxystilbenes. Influence of non-planarity in styrene and stilbene derivatives IV" *Recueil des Travaux Chimiques des Pays-Bas* 80:775-791 (1961).

Lagrost et al., "Opposite Effects of Cholesteryl Ester Transfer Protein and Phospholipid Transfer Protein on the Size Distribution of Plasma High Density Lipoproteins" *J. Biol. Chem.* 271:19058-19065 (1996).

Lamon-Fava, "Genistein activates apolipoprotein A-I gene expression in the human hepatoma cell line Hep G2" *J. Nutrition* 130:2489-2492 (2000).

Landshulz et al., "Regulation of Scavenger Receptor, Class B, Type I, a High Density Lipoprotein Receptor, in Liver and Steroidogenic Tissues of the Rat" *J. Clin. Invest.* 98:984-995 (1996).

Lin et al., "Potential bioreductive alkylating agents. 7. Antitumor effects of phenyl-substituted 2-chloromethyl-3-phenyl-1,4-naphthoquinones" *J. Med. Chem.* 19(11):1336-1338 (1976).

Lin et al., "Chemoprevention of Cancer and Cardiovascular Disease by Resveratrol" *Proc. Natl. Sci. Counc. ROC (B)* 23:99-106 (1999).

Lin et al., "Solvent Effects on Aza-Anionic Cycloaromatization of 2-(2-Substituted-Ethynyl)Benzonitriles" *J. Chinese Chem. Soc.* 48:211-214 (2001).

Lin et al., "The Role of Absorption, Distribution, Metabolism, Excretion and Toxicity in Drug Recovery" *Curr. Top. Med. Chem.* 3:1125-1154 (2003).

Linnell, W.H., "Isomers of stilbestrol. II." *Q. J. Pharm. Pharmacol.* 15:384-388 (1942).

Lopez et al., "The Synthesis of Substituted 2-Aryl-4(3H)-quinazolinones using NaHSO3/DMA. Steric Effect Upon the Cyclisation-Dehydrogenation Step" *J. Chem. Research (S)* pp. 258-259 (2000).

Maher et al.,"Lipoprotein (a) and coronary heart disease" *Curr. Opin. Lipidol.* 6:229-235 (1995).

Mahto et al., "Synthesis of 3-Aryl-7-hydroxy Isochromenes" *Asian J. Chem.* 11(2):431-435 (1999).

Manach et al., "Polyphenols and prevention of cardiovascular diseases" *Curr. Opin. Lipidol.* 16:77-84 (2005).

Marks, F., "Epidermal Growth Control Mechanisms, Hyperplasia, and Tumor Promotion in the Skin" *Cancer Res.* 36:2636-2343 (1976).

Martin et al.,"Modified Flavinoids As Strong Photoprotecting UV-Absorbers and Antioxidants" *Strategies for Safe Food*. Eklund, T. et al.,(Eds.) vol. 1, pp. 288-291 (2003).

Mckee et al., "Some Basically Substituted Quinazolines" *J. Am. Chem. Soc.* 68(10):1902-1903 (1946).

Meckes et al., "The effects of chrysin and pinostrobin, 2 flavonoids isolated from teloxys graveolens leaves, on isolated guinea-pig ileum" *Phytomedicine* 5(6):459-463 (1998).

Melani, F. et al., "Tricyclic heterocyclic systems: pyrazolo[5',4':4,5]- and pyrazolo-[3',4':4,5]pyrano[2,3-B]pyridine derivatives" *J. Heterocyclic Chem.* 25:1367-1371 (1988).

Middleton et al., "Quercetin inhibits lipopolysaccharide-induced expression of endothelial cell intracellular adhesion molecule-1" *Int. Archives of Allergy and Immunology* 107(1/3):435-436 (1995).

Mondal et al., "Two-Stage Chemical Oncogenesis in Cultures of C3H/10T1/2 Cells" *Cancer Res.* 36:2254-2260 (1976).

Nigam et al., "Synthesis and Pharmacological Screening of Some New 2-(Phenyl/Chloromethyl)-3-[4 (N, N-Disubstituted Aminocarbonyl) Phenyl]-8-Substituted-4 (3H)-Quinazolones" *Indian Drugs* 27(4):238-243 (1990).

Nissen et al., "Effect of Recombinant ApoA-I Milano on Coronary Atherosclerosis in Patients with Acute Coronary Syndroms: A Randomized Controlled Trial" *JAMA* 290(17):2292-2300 (2003).

Nourooz-Zadeh, "Ferrous Ion Oxidation in Presence of Xylenol Orange for Detection of Lipid Hydroperoxides in Plasma" *Methods Enzymol.* 300:58-62 (1999).

Ohtomo et al., "Comparative activities of daidzein metabolites, equol and O-desmethylangolensin, on bone mineral density and lipid metabolism in ovariectomixed mice and in osteoclast cell cultures" *Eur. J. Nutr.* 47(5):273-279 (2008).

Ordovas, J.M., "Gene-diet interaction and plasma lipid responses to dietary intervention" *Biochem. Soc. Trans.* 30(2):68-73 (2002).

Parra et al., "A Case-Control Study of Lipoprotein Particles in Two Populations at Contrasting Risk for Coronary Heart Disease" *Artetioscler Thromb.* 12:701-707 (1992).

Patani et al.,"Bioisosterism: A rational approach in drug design" *Chem. Rev.* 96(8):3147-3176 (1996).

Pearson et al., "The Ortho Bromination of Phenols" *J. Org. Chem.* 32:2358-2360 (1967).

Pettit et al., "Antineoplastic Agents. 465. Structural Modification of Resveratrol: Sodium Resverastatin Phosphate" *J. Med. Chem.* 45:2534-2542 (2002).

Plump et al., "Human apolipoprotein A-I gene expression increases high density lipoprotein and suppresses atherosclerosis in the apolipoprotein E-deficient mouse" *Proc. Natl. Acad. Sci. USA* 91:9607-9611 (1994).

Quinones et al., "The egr-1 gene is induced by DNA-damaging agents and non-genotoxic drugs in both normal and neoplastic human cells" *Life Sciences* 72(26):2975-2992 (2003).

Ragione et al., "Antioxidants induce different phenotypes by a distinct modulation of signal transduction" *FEBS Letters* 523:289-294 (2002).

Ragione et al., "p21$^{CIP}$ 1 Gene Expression Is Modulated by Egr1: A Novel Regulatory Mechanism Involved in the Resveratrol Antiproliferative Effect" *J. Biol. Chem.* 278:23360-23368 (2003).

Rajakumar, P. et al.,"TiCI$_4$, Dioxane—A facile and efficient system for de-O-benzylation, de-O-allylation, and de-O-xylylation of phenolic ethers" *Synthetic Communications* 33(22):3891-3896 (2003).

Raun et al., "Apolipoprotein A-I possesses an anti-obesity effect associated with increase of energy expenditure and upregulation of UCP1 in brown fat" *J. Cell. Mol. Med.* (2010). "Postprint"; 10.1111/j.1582.4934.2010.01045.x.

Rice-Evans, "Flavonoids and Isoflavones: Absorption, Metabolism, and Bioactivity" *Free Radical Biol. Med.* 36:827-828 (2004).

Richtzenhain, H. "Estrogenic stilbene and diphenylethane derivatives. II." *Chemische Berichte* 82:405-407 (1949).

Rigotti et al., "Regulation by Adrenocorticotropic Hormone of the in Vivo Expression of Scavenger Receptor Class B Type I (SR-BI), a High Density Lipoprotein Receptor, in Steroidogenic Cells of the Murine Adrenal Gland" *J. Biol. Chem.* 271:33545-33549 (1996).

Rimando et al., "Pterostilbene, a New Agonist for the Peroxisome Proliferator-Activated Receptor α-Isoform, Lowers Plasma Lipoproteins and Cholesterol in Hypocholesterolemic Hamsters" *Journal of Agricultural and Food Chemistry* 53(9):3403-3407 (2005).

Rodriguez et al., "Novel Effects of the Acyl-Coenzyme A: Cholesterol Acyltransferase Inhibitor 58-035 on Foam Cell Development in Primary Human Monocyte-Derived Macrophages" *Arterioscler. Thromb. Vasc. Biol.* 19:2199-2206 (1999).

Rose et al., "Oxygen Heterocycles. XIII. From 3-Arylisocoumarins to 3-Arylisoquinolines and 4-Aryl-5H-2,3-Benzodiazepines" *J. Chem. Soc. [Section] C: Organic* 17:2205-2208 (1968).

Rubin et al., "Expression of Human Apolipoprotein A-1 in Transgenic Mice Results in Reduced Plasma Levels of Murine Apolipoprotein A-1 and the Appearance of Two New High Density Lipoprotein Size Subclasses" *Proc. Natl. Acad. Sci. USA* 88:434-438 (1991).

Rubin et al., "Inhibition of Early Atherogenesis in Transgenic Mice by Human Apolipoprotein AI" *Nature* 353:265-267 (1991).

Rubins et al., "Reduction in Stroke with Gemfibrozil in Men with Coronary Heart Disease and Low HDL Cholesterol" *Circulation* 103:2828-2833 (2001).

Sarkhel et al., "3-Arylisocoumarin: Synthesis of 3-(4-Methoxyphenyl)Isocoumarin" *J. Indian Chem. Soc.* 53:915-916 (1976).

Schiess et al., "Thermolytic Ring Opening of Acyloxybenzocyclobutenes: An Efficient Route to 3-Substitute Isoquinolines" *Tetrahedron Lett.* 26:3959-3962 (1985).

Schmutz et al., "Synthese von basisch substituierten Chromonen" *Helv. Chim. Acta* 620 (1953) (German), Abstract.

Schork, N., "Genetics of Complex Disease" *Am. J. Respir. Crit. Care Med.* 156(4):S103-109 (Oct. 1997).

Schultz, T.P. et al.,"Role of stilbenes in the natural durability of wood: fungicidal structure-activity relationships" *Phytochemistry* 29(5):1501-1507 (1990).

Shah et al., "Effects of Recombinant Apolipoprotein A-I Milano on Aortic Atherosclerosis in Apolipoprotein E-Deficient Mice" *Circulation* 97(8):780-785 (1998).

Shapiro et al., "Micro Assay for 3-Hydroxy-3-Methylglutaryl-CoA Reductase in Rat Liver and L-Cell Fibroblasts" *Biochim. Biophys. Acta* 370:369-377 (1974).

Sharrett et al., "Associations of Lipoprotein Cholesterols, Apolipoproteins A-I and B, and Triglycerides with Carotid Atherosclerosis and Coronary Heart Disease" *Arterioscler. Thromb.* 14:1098-1104 (1994).

Sieber, R.H., "Reactions of chloroacetaldehyde with aromatic hydrocarbons, phenols, and phenol ethers" *Justus Liebigs Annalen der Chemie* 730:31-46 (1969) (German).

Sliwa, H. et al.,"Tautomerie entre structures α-aleoxy-enaminocetone et β-ceto iminoether presentee par les piperidines resultant de la semihydrogenation d'alcoxy-2-acyl-3 pyridines" *J. Heterocyclic Chem.* 16:939 (1979) (French).

Slowing et al., "Anti-Inflammatory Activity of Leaf Extracts of Eugenia Jambos in Rats" *J. Ethnopharmacol.* 43:9-11 (1994).

Smyth, M.S. et al.,"Non-amine based analogues of lavendustin A as protein-tyrosine kinase inhibitors" *J. Med. Chem.* 36(20):3010-3014 (1993).

Sun et al., "In Vitro Testing of Drug Absorption for Drug 'Developability' Assessment: Forming an Interface Between in Vitro Preclinical Data and Clinical Outcome" *Curr. Opin. Drug Discov. Devel.* 7:75-85 (2004).

Suryadevara et al., "Association of Abnormal Serum Lipids in Elderly Persons with Artherosclerotic Vascular Disease and Demetia. Artheroslerotic Vascular Disease Without Demetia, Demetia Without Artherosclerotic Vascular Disease, and No Dementia or Artherosclerotic Vascular Disease" *J. Gerontol. Med. Sci.* 58(9):M859-861 (2003).

Tait et al., "Synthesis and Free Radical Scavenging Activity of 4-(2H-1,2,4-Benzothiadiazine-1,1-dioxide-3-y1)-2,6-bis(1,1-dimethylethyl)phenols" *Tetrahedron* 52(38):12587-12596 (1996).

Talbert, "Current Recommendations for the Treatment of Dyslipidemia" *Pharm. Ther.* 29:104 (2004).

Tanne et al., "High-Density Lipoprotein Cholesterol and Risk of Ischemic Stroke Mortaility" *Stroke* 28:83-87 (1997).

Tardiff et al., "Probucol and Multivitamins in the Prevention of Restenosis After Coronary Angioplasty" *N. Engl. J. Med.* 337:365-367 (1997).

Theriault et al., "Modulation of hepatic lipoprotein synthesis and secretion by taxifolin, a plant flavonoid," *J. Lipid Res.* 41:1969-1979 (2000).

Toth et al., "Therapeutic Interventions Targeted at the Augmentation of Reserve Cholesterol Transport" *Curr. Opin. Cardiol.* 19:374-379 (2004).

Tovar et al., "Pyrylium Salts Via Electrophilic Cyclization: Applications for Novel 3-Arylisoquinoline Syntheses" *J. Org. Chem.* 64:6499-6504 (1999).

Tudan, "Selective Inhibition of Protein Kinase C, Mitogen-Activated Protein Kinase, and Neutrophil Activation in Response to Calcium Pyrophosphate Dihydrate Crystals, Formyl-Methionyl-Leucyl-Phenylalanine, and Phorbol Ester by O-(Chloroacetyl-carbamoyl) Fumagillol (AGM-01470; TNP-470)" *Biochem. Pharmacol.* 58:1869-1880 (1999).

Utermann, "The Mysteries of Lipoprotein(a)" *Science* 246:904-910 (1989).

Van Der Goot et al., "The Growth-Inhibitory Action of Some 1-Aminoisoquinolines and Related Compounds on *Mycoplasma gallisepticum*" *Eur. J. Med. Chem.* 10:603-606 (1975).

Varin et al., "Enzymatic Assay for Flavonoid Sulfotransferase" *Anal. Biochem.* 161:176-180 (1987).

Vippagunta et al., "Crystalline solids" *Adv. Drug Delivery Rev.* 48:3-26 (2001).

Walle, "Absorption and Metabolism of Flavonoids" *Free Radical Biol. Med.* 36(7):829-837 (2004).

Webster Ninth New Collegiate Dictionary, Definition of 'Prevent', 1 page (2000).

Wei et al., "Total Cholesterol and High Density Lipoprotein Cholesterol as Important Predictors of Erectile Dysfunction" *Am. J. Epidemiol.* 140(10):930-937 (1994).

Welsh et al., "Dyslipidemia in Diabetic Patients" *Prospectives in Cardiology* Aug. 2002, pp. 40-48.

Wölle et al., "Selective inhibition of tumor necrosis factor-induced vascular cell adhesion molecule-1 gene expression by a novel flavonoid: lack of effect on transcription factor NF-kappa-B" *Arterioscler. Thromb. Vasc. Biol.* 16(12):1501-1508 (1996).

Wurm et al., "1,4-Naphthoquinones, XXVI: Phenyl-1,4-naphthoquinone derivatives with the hydroxylation patterns of bioflavonoids" *Pharmazie* 52(10):739 (1997) (German), Abstract.

Wurm, "1 4 naphthoquinones XXI. 2-3 5 di-*tert*-butyl-4-hydroxyphenyl-1 4-naphtoquinones as 5 lipozxygenase inhibitors" *Archiv. der Pharmazie* 324(8):491-495 (1991) (German), Abstract.

Yamakoshi et al., "Isoflavone aglycone-rich extract without soy protein attenuates atherosclerosis development in cholesterol-fed rabbits" *Journal of Nutrition* 130(8), printed pp. 1-19 (2000).

Yardley et al., "In vitro activity of diospyrin and derivatives against *Leishmania donovani, Trypanosome cruzi* and *Trypanosoma brucei brucei*" *Phytotherapy Research* 10(7):559-562 (1996).

Yoshioka, N. et al., "Semiempirical Investigation of Stilbene-Linked Diradicals and Magnetic Study of Their Bis(*N-tert*-butylnitroxide) Variants" *J. Org. Chem.* 59(15):4272-4280 (1994).

Office Action in U.S. Appl. No. 11/254,420, mailed Aug. 5, 2008.
Office Action in U.S. Appl. No. 11/254,420, mailed Mar. 3, 2009.
Office Action in U.S. Appl. No. 11/254,420, mailed Sep. 28, 2009.
Office Action in U.S. Appl. No. 11/254,420, mailed Feb. 2, 2010.
Notice of Allowance in U.S. Appl. No. 11/254,420, mailed Jul. 26, 2010.
Office Action in U.S. Appl. No. 11/255,103: Restriction Requirement, mailed Mar. 26, 2008.
Office Action in U.S. Appl. No. 11/255,103, mailed Sep. 24, 2008.
Office Action in U.S. Appl. No. 11/255,103 mailed Aug. 31, 2009.
Office Action in U.S. Appl. No. 11/255,103, mailed Mar. 31, 2010.
Office Action in U.S. Appl. No. 11/255,103, mailed Nov. 10, 2010.
Notice of Allowance in U.S. Appl. No. 11/255,103, mailed Jun. 7, 2011.
Office Action in U.S. Appl. No. 11/990,162: Restriction Requirement, mailed Jul. 10, 2009.
Office Action in U.S. Appl. No. 11/990,162, mailed Oct. 14, 2009.
Office Action in U.S. Appl. No. 11/990,162, mailed Apr. 1, 2010.
Office Action in U.S. Appl. No. 11/990,162, mailed Dec. 28, 2010.
Office Action in U.S. Appl. No. 11/670,238: Restriction Requirement, mailed Mar. 31, 2010.
Office Action in U.S. Appl. No. 11/670,238: Restriction Requirement, mailed Jul. 20, 2010.
Office Action in U.S. Appl. No. 11/670,238, mailed Oct. 7, 2010.
Office Action in U.S. Appl. No. 11/670,238, mailed Apr. 19, 2011.

METHODS OF PREPARING QUINAZOLINONE DERIVATIVES

This application claims the benefit of U.S. Provisional Application No. 61/075,952, filed Jun. 26, 2008, which is incorporated herein by reference in its entirety.

The present disclosure relates to methods of preparing quinazolinone derivatives, which are useful for regulating the expression of apolipoprotein A-I (ApoA-I) and in the treatment and prevention of cardiovascular disease and related disease states, such as, for example, atherosclerosis.

Epidemiologic data demonstrate an inverse relationship between circulating levels of high-density lipoprotein cholesterol (HDL-C) and the incidence of clinically significant atherosclerosis. Each 1 mg/dL increment in the HDL-C serum level is associated with a 2-3% decrement in cardiovascular risk; a 1% reduction in LDL-C reduced cardiovascular risk by 2% (Gordon et al. (1997) *Am. J. Med.* 62, 707-714). Experimental evidence further supports the protective effect of HDL-C against cardiovascular disease. For example, in subjects with low HDL-C, administration of gemfibrozil resulted in a 6% increase in the HDL-C level and a corresponding 22% reduction of the coronary heart disease (CHD) risk (Rubins et al., (1999) *N. Engl. J. Med.* 341, 410-418). Observations in genetic disorders associated with low HDL-C due to reduced ApoA-I expression also indicate a link between elevated risk of CHD and low HDL-C.

HDL-C appears to exert its anti-atherogenic effect by mediating reverse cholesterol transport (RCT), in which cholesterol is recruited from peripheral tissues and transported to the liver. In addition, HDL-C also possesses pleiotropic biological properties that contribute to its antiatherogenic effects, such as anti-inflammatory, anti-oxidant, and anti-thrombotic activities. HDL-C exists in two main forms, one containing both apolipoprotein A-I (ApoA-I) and apolipoprotein A-II (ApoA-II), and the other containing ApoA-I without ApoA-II (Schultz et al. (1993) *Nature* 365, 762-764). The cardioprotective effect of HDL-C is primarily, but not exclusively, attributable to ApoA-I.

Clinical and experimental data suggest that the production of ApoA-I is an important determinant of circulating HDL-C. For example, persons with familial hyperalphalipoproteinemia (elevated ApoA-I) appear to be protected from atherosclerosis, while those deficient in ApoA-I (hypoalphalipoproteinemia) show accelerated cardiovascular disease. In addition, various experimental manipulations to increase production of ApoA-I are associated with reduced atherogenicity. For example, human ApoA-I is protective in transgenic animal models (Shah et al. (1998) *Circulation* 97, 780-785; Rubin et al. (1991) *Nature* 353, 265-267), and treatment with ApoA-I$_{Milano}$ prevents atherosclerotic lesions and leads to regression of atherosclerotic plaques in human patients (Nissen et al. (2003) *JAMA* 290, 2292-2300). Further lines of research demonstrate that ApoA-I plays a role in enhancing reverse cholesterol transport, attenuating oxidative stress, increasing paraoxonase activity, enhancing anticoagulant activity, and increasing anti-inflammatory activity (Andersson (1997) *Curr. Opin. Lipidol.* 8, 225-228). Accordingly, ApoA-I is an attractive target for therapeutic intervention.

Currently available therapeutic agents that increase the plasma concentration of ApoA-I, for example, recombinant ApoA-I or peptides that mimic ApoA-I, have potential drawbacks with respect to, e.g., stability during storage, delivery of active product, and in vivo half-life. Thus, small molecule compounds that up-regulate the production of endogenous ApoA-I, such as, for example, up-regulators of ApoA-I expression, would be attractive as new therapeutic agents for cardiovascular disease.

The methods of the present invention provide improved procedures for preparing up-regulators of ApoA-I expression. For the disclosed compounds of Formulae I, VI and VIII, alkylation of the phenol starting material with ethylene carbonate, rather than alkylating agents of known procedures, is more efficient, and thus less expensive on a large scale. The coupling procedures of the invention described herein to form the quinazolinones result in lower levels of impurities and increased yield of the final compounds.

DEFINITIONS

It should be noted that, as used in this specification and the appended claims, the singular forms "a," "an," and "the" include plural referents unless the content clearly dictates otherwise. Thus, for example, reference to a method containing "a compound" includes a mixture of two or more compounds. It should also be noted that the term "or" is generally employed in its sense including "and/or" unless the content clearly dictates otherwise. Unless otherwise specified, the chemical groups refer to their unsubstituted and substituted forms.

The terms "compound of Formula I", "compound of Formula VI", and "compound of Formula VIII" are intended to include any stereoisomer, tautomer, and/or pharmaceutically acceptable salt as defined herein. Compounds of Formula I, Formula VI, and Formula VIII also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to. Compounds of Formula I, Formula VI, and Formula VIII also include pharmaceutically acceptable forms of the recited compounds, including chelates, non-covalent complexes, prodrugs, and mixtures thereof.

As noted above, prodrugs also fall within the scope of compounds of Formula I, Formula VI, and Formula VIII. In some embodiments, the "prodrugs" described herein include any compound that becomes a compound of Formula I, Formula VI and/or Formula VIII when administered to a patient, e.g., upon metabolic processing of the prodrug. Examples of prodrugs include derivatives of functional groups, such as a carboxylic acid group, in the compounds of Formula I, Formula VI and/or Formula VIII. Exemplary prodrugs of a carboxylic acid group include, but are not limited to, carboxylic acid esters such as alkyl esters, hydroxyalkyl esters, arylalkyl esters, and aryloxyalkyl esters.

A "solvate" is formed by the interaction of a solvent and a compound. The terms "compound of Formula I", "compound of Formula VI", and "compound of Formula VIII" are intended to include solvates of compounds. Similarly, "salts" includes solvates of salts. Suitable solvates are pharmaceutically acceptable solvates, such as hydrates, including monohydrates and hemi-hydrates.

A "chelate" is formed by the coordination of a compound to a metal ion at two (or more) points. The term "compound"

is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound".

The compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

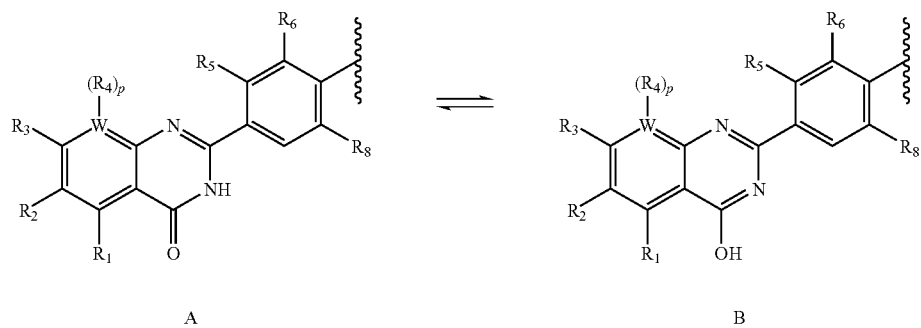

As used herein, the terms have the meaning given in US Patent Publication No. 2006/0205767 at pp. 3-7, which disclosure is incorporated herein by reference. The term "radical" used in these definitions refers to a substituent group or variable group.

In addition, the term "imido" refers to a group having the structure —C(O)NC(O)—R$_z$, where R$_z$ can be selected from alkyl, alkenyl, alkynyl, aryl, arylalkyl, cycloalkyl, haloalkyl, heteroaryl, and heterocyclyl.

One embodiment provides a method of preparing a compound of Formula I:

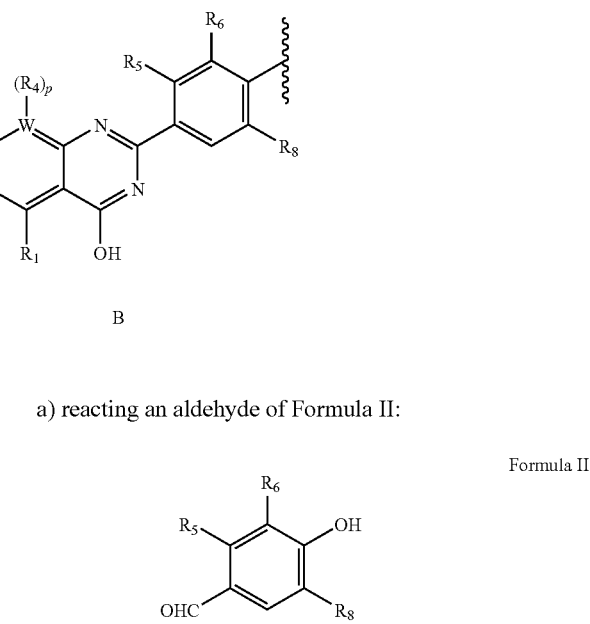

Formula I and solvates, hydrates, tautomers, and pharmaceutically acceptable salts thereof, wherein:

$R_1$, $R_2$, $R_3$, and $R_4$ are each independently selected from alkoxy, alkyl, amido, aryloxy, cycloalkyl, halogen, heterocyclyl, hydrogen, and nitro;

$R_6$ is selected from alkyl, alkoxy, and halogen;

$R_5$ is hydrogen, or $R_5$ and $R_6$ may be taken together with the carbon atoms to which they are attached, to form a ring selected from aryl, cycloalkyl, and heterocycyl;

$R_8$ is selected from alkyl, alkoxy, halogen, and hydrogen;

W is C or N, where if W is N, then p is 0, and if W is C, then p is 1; comprising a) reacting an aldehyde of Formula II:

Formula II wherein $R_5$, $R_6$ and $R_8$ are as defined above, with ethylene carbonate to form a compound of Formula III:

Formula III b) reacting the compound of Formula III with a compound of Formula IV:

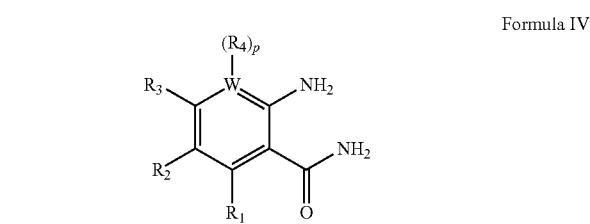

Formula IV wherein $R_1$, $R_2$, $R_3$, and $R_4$ are as defined above, to form the compound of Formula I.

In one embodiment, $R_1$ and $R_3$ can each be independently selected from alkoxy, alkyl, halogen, and hydrogen. In another embodiment, $R_1$ and $R_3$ can each be independently selected from chloro, hydrogen, methoxy, and methyl. In a further embodiment, $R_1$ and $R_3$ can each be methoxy.

In one embodiment, $R_2$ can be selected from bromo, hydrogen, methoxy, and methylamido. In a further embodiment, $R_2$ can be hydrogen. In one embodiment, W can be N. In another embodiment, W can be C and $R_4$ can be hydrogen.

In one embodiment, $R_6$ can be selected from chloro, methoxy, and methyl. In another embodiment, $R_6$ can be methyl. In another embodiment, $R_6$ and $R_8$ can be each independently selected from alkyl and halogen. In one embodiment, $R_8$ can be selected from chloro, hydrogen, methoxy, and methyl. In a further embodiment, $R_6$ and $R_8$ can be each methyl.

In one embodiment, the compound of Formula I can be selected from:
2-(4-(2-hydroxyethoxy)-3,5-dimethylphenyl)quinazolin-4(3H)-one;
2-(3-chloro-4-(2-hydroxyethoxy)phenyl)-5,7-dimethoxyquinazolin-4(3H)-one;
2-(4-(2-hydroxyethoxy)-3-methoxyphenyl)-5,7-dimethoxyquinazolin-4(3H)-one;
2-(4-(2-hydroxyethoxy)-3,5-dimethylphenyl)-5,7-dimethoxyquinazolin-4(3H)-one;
2-(4-(2-hydroxyethoxy)-3,5-dimethylphenyl)-6,7-dimethoxyquinazolin-4(3H)-one;
2-(4-(2-hydroxyethoxy)-3,5-dimethylphenyl)-5,7-dimethoxypyrido[2,3-d]pyrimidin-4(3H)-one;
N-(2-(4-(2-hydroxyethoxy)-3,5-dimethylphenyl)-4-oxo-3,4-dihydroquinazolin-6-yl)acetamide;
2-(4-(2-hydroxyethoxy)-3,5-dimethylphenyl)-5,7-dimethylquinazolin-4(3H)-one;
5,7-dichloro-2-(4-(2-hydroxyethoxy)-3,5-dimethylphenyl)quinazolin-4(3H)-one;
2-(4-(2-hydroxyethoxy)-3,5-dimethylphenyl)-6-methoxyquinazolin-4(3H)-one;
2-(4-(2-hydroxyethoxy)-3,5-dimethylphenyl)-5-methoxyquinazolin-4(3H)-one;
6-bromo-2-(4-(2-hydroxyethoxy)-3,5-dimethylphenyl)quinazolin-4(3H)-one; and
2-(4-(2-hydroxyethoxy)-3-methylphenyl)-5,7-dimethoxyquinazolin-4(3H)-one, and solvates, hydrates, tautomers, and pharmaceutically acceptable salts thereof.

In another embodiment, the compound of Formula I is 2-(4-(2-hydroxyethoxy)-3,5-dimethylphenyl)-5,7-dimethoxyquinazolin-4(3H)-one, or a solvate, hydrate, tautomer, or pharmaceutically acceptable salt thereof.

In one embodiment, a reaction step can be performed in a large scale. In one embodiment, "large scale" refers to the use of at least 50 grams of a starting material, intermediate or reagent, such as the use of at least 100 grams, at least 500 g, at least 1 kg, at least 10 kg, at least 25 kg, at least 50 kg, at least 100 kg, at least 250 kg, or at least 500 kg.

In one embodiment, the aldehyde of Formula II:

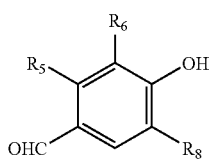

Formula II can be combined with ethylene carbonate in a solvent, such as dimethylformamide, dichloromethane, isopropanol, methanol, tetrahydrofuran, toluene, xylene and water, and stirred at elevated temperature, such as 110° C., to form the alkylated compound of Formula III. This compound can be purified by crystallization from, for example, dichloromethane/heptane. Use of ethylene carbonate allows for improved control of the alkylation process and is much more cost effective than other known methods.

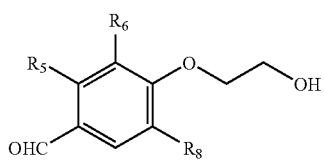

Formula III

The compound of Formula III can then be combined with a compound of Formula IV in N,N-dimethylacetamide (DMAC). Other suitable solvents include acetonitrile, benzene and methanol.

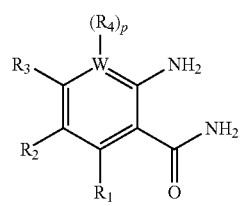

Formula IV

Sodium bisulfite can then be added in portions, such as one-third portions, with heating, e.g., at approximately 115° C. An acid, such as p-toluenesulfonic acid monohydrate, can be added with the first portion of sodium bisulfite. The reaction can be stirred for at least about 90 minutes, such as 90-105 minutes, between addition of the portions. Gradual addition of the portions over at least a 4 hour period significantly reduces the amount of impurities present in the final compound of Formula I, some of which are otherwise difficult to remove during the purification stage of the process.

Upon completion of the reaction, the reaction mixture can be cooled and the resulting product can be recrystallized from, for example, DMAC/heptane. Alternatively, the unpurified product can be triturated with acetone. In another embodiment, this first purification step can be omitted. Following the first purification step, the product can then be recrystallized from ethanol/water to provide the compound of Formula I.

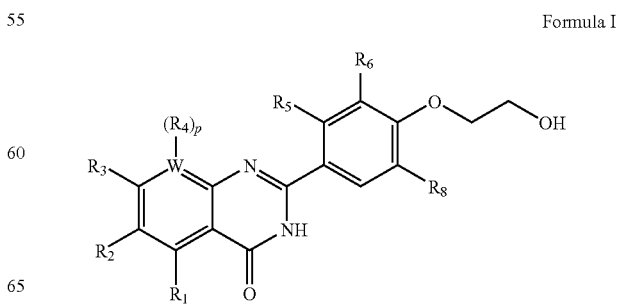

Formula I

In a further embodiment, the compound of Formula I can be treated with an isocyanate of Formula V

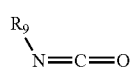

Formula V and a base, such as triethylamine or Hunig's base, to form a carbamate compound of Formula VI.

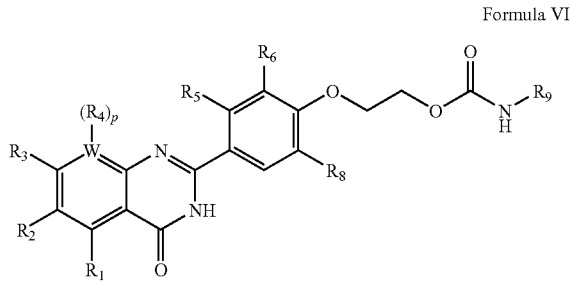

Formula VI

In one embodiment, $R_9$ can be selected from alkyl, aryl, cycloalkyl, heteroaryl, and heterocyclyl. In another embodiment, $R_9$ can be aryl substituted with one or more groups selected from alkoxy, alkyl, and halogen. In another embodiment, the compound of Formula VI is 2-(4-(5,7-dimethoxy-4-oxo-3,4-dihydroquinazolin-2-yl)-2,6-dimethylphenoxy)ethyl cyclohexylcarbamate, or a solvate, hydrate, tautomer, or pharmaceutically acceptable salt thereof.

In another embodiment, the compound of Formula I can be treated with a reagent to form a leaving group $R_{10}$, as shown in Formula VII. The leaving group $R_{10}$ may be selected from halogen, sulfonyl, and phosphonium, such as chloride, methanesulfonyl, p-toluenesulfonyl, and triphenylphosphonium. The reagent can be selected from thionyl chloride, methanesulfonyl chloride, p-toluenesulfonyl chloride, and $PPh_3$/diethyl azodicarboxylate.

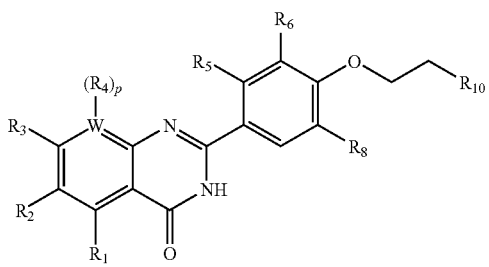

Formula VII

The compound of Formula VII may then be treated with a nucleophilic reagent, such as an alkoxide, an amine, or a heterocycle having at least one nitrogen, including imido compounds, to provide a compound of Formula VIII. Alternatively, when $R_{10}$ is triphenylphosphonium, the compound of Formula VII can be treated in situ with $HN_3$ followed by reduction with reagents such as Pd—$C/H_2$ to form an intermediate amine, which can then be treated with an acylating agent to form the compound of Formula VIII having an amido group or an imido group. As shown in Formula VIII, $R_{11}$ can be selected from alkoxy, amido, amino, imido, and heterocyclyl. In one embodiment, $R_{11}$ is selected from methoxy, methylamino, morpholino, piperazino, and piperidino.

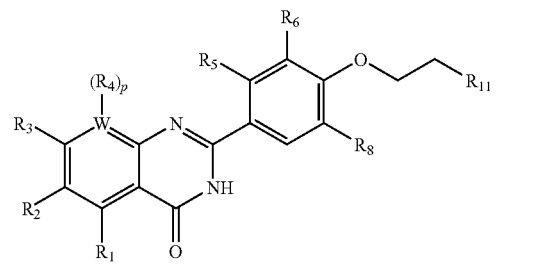

Formula VIII

In one embodiment, a compound of Formula I can be treated with methanesulfonyl chloride and triethylamine in dichloromethane to form the corresponding mesylate. The mesylate may then be treated with an amine, such as methylamine, in refluxing ethanol to give the compound of Formula VIII. In a further embodiment, the compound of Formula VIII is 2-(3,5-dimethyl-4-(2-(methylamino)ethoxy)phenyl)-5,7-dimethoxy-quinazolin-4(3H)-one, or a solvate, hydrate, tautomer, or pharmaceutically acceptable salt thereof.

In another embodiment, a compound of Formula VIII can be prepared by reacting the aldehyde of Formula II with ethylene carbonate to provide the compound of Formula III. The compound of Formula III can then be reacted with a reagent to create a leaving group $R_{12}$ on the compound of Formula IX.

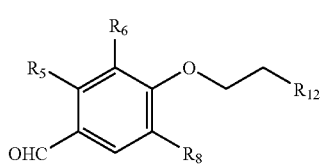

Formula IX

In one embodiment, $R_{12}$ can be selected from halogen, sulfonyl, and phosphonium, such as chloride, methanesulfonyl, p-toluenesulfonyl, and triphenylphosphonium. In another embodiment, the reagent is selected from thionyl chloride, methanesulfonyl chloride, p-toluenesulfonyl chloride, and $PPh_3$/diethyl azodicarboxylate.

The compound of Formula IX may be treated with an nucleophilic reagent, such as an alkoxide, amine or a heterocycle having at least one nitrogen, including imido compounds, to provide a compound of Formula X. Alternatively, when $R_{12}$ is triphenylphosphonium, the compound of Formula VII can be treated in situ with $HN_3$ followed by reduction with reagents such as Pd—$C/H_2$ to form an intermediate amine, which can be treated with an acylating agent to form the compound of Formula VIII having an amido group or an imido group.

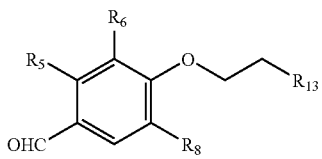

Formula X

As shown in Formula X, $R_{13}$ can be selected from alkoxy, amido, amino, imido, and heterocyclyl. In one embodiment, $R_{13}$ is selected from methoxy, methylamino, morpholino, piperazino, and piperidino.

The compound of Formula X may then be condensed with a compound of Formula IV to form the compound of Formula VIII. In one embodiment, $R_6$ and $R_8$ are each methyl. In another embodiment, $R_1$ and $R_3$ are each hydrogen. In a further embodiment, the compound of Formula VIII is 2-(3,5-dimethyl-4-(2-morpholinoethoxy)phenyl)quinazolin-4(3H)-one, or a solvate, hydrate, tautomer, or pharmaceutically acceptable salt thereof.

EXAMPLES

The invention is further illustrated by the following non-limiting examples, wherein the following abbreviations have the following meanings. If an abbreviation is not defined, it has its generally accepted meaning.

Abbreviations used herein denote the following compounds, reagents and substituents: acetonitrile (MeCN); diisopropylethylamine (DIPEA); N,N-dimethylacetamide (DMAC); dimethylformamide (DMF); ethyl acetate (EtOAc); methanesulfonyl anhydride ($Ms_2O$); methanesulfonyl chloride (MsCl); p-toluenesulfonic acid (p-TsOH); and triethylamine ($Et_3N$).

Example 1

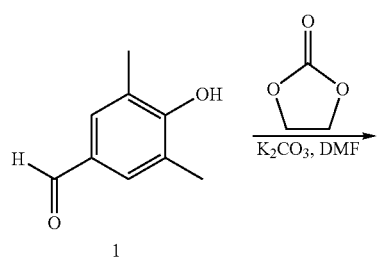

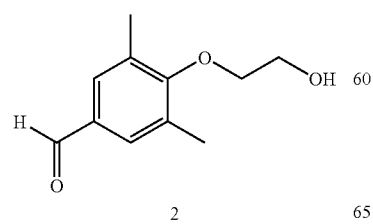

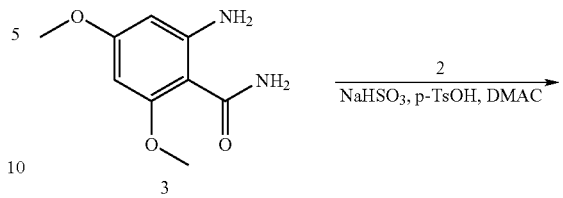

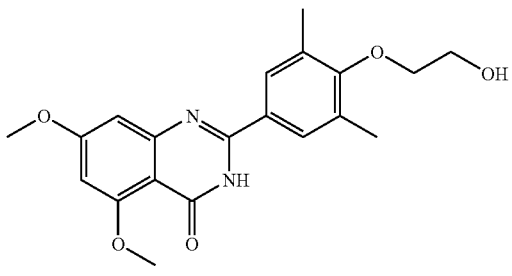

2-(4-(2-hydroxyethoxy)-3,5-dimethylphenyl)-5,7-dimethoxyquinazolin-4(3H)-one (4)

The starting material 4-hydroxy-3,5-dimethylbenzaldehyde (1; 70 kg), $K_2CO_3$ (9.8 kg) and DMF (133 kg) were mixed and stirred at 110° C. under nitrogen. Ethylene carbonate (45.6 kg) in DMF (46 kg) was added to the mixture over a period of 4 hours, using a diaphragm pump. The reaction mixture was stirred at 110° C. for 12 hours, until less than 5% of the starting material 1 remained. The reaction mixture was cooled to 25° C. and water (1300 kg) was added followed by a mixture of dichloromethane and heptane (3V/2V; 1300 kg). The mixture was agitated for 30 minutes. The organic layer was isolated and the aqueous layer was back extracted with a mixture of dichloromethane and heptane (3V/2V; 1300 kg). The combined organic layers were washed with aqueous sodium hydroxide (3 M; 460 kg), followed by three washes with water (3×710 kg), and dried over sodium sulfate (60 kg). Dichloromethane was removed from the dried organic layer by distillation, keeping the temperature below 40° C. Heptane (260 kg) and seed crystals were added to initiate crystallization and the mixture was stirred at 20° C. for 2 hours. The mixture was filtered, washed with heptane (60 kg), and dried under vacuum until constant weight to afford intermediate 2 (71.3 kg, 78.8%). $^1$H-NMR (DMSO-$d_6$): δ 9.82 (1H), 7.54 (2H), 4.96 (1H), 3.85 (2H), 3.74 (2H), 2.29 (6H).

Intermediate 2 (58.74 kg), N,N-dimethylacetamide (280 kg), and starting material 3 (56.00 kg) were combined and p-toluenesulfonic acid monohydrate (5.90 kg) and ⅓ of the required sodium bisulfite (24.1 kg) were added. The mixture was heated to 115° C. and stirred for 90-105 minutes before the second ⅓ of the required sodium bisulfite (24.1 kg) was added. The remaining sodium bisulfite (24.1 kg) was added after another 90-105 minutes. The reaction mixture was stirred at 115° C. until the reaction was complete as determined by HPLC (approximately 1 hour, less than 4% of intermediate 2 remaining). The reaction mixture was cooled to 25° C. and added to water (1770 kg). The mixture was stirred at 20° C. for 6 hours to complete the crystallization. The crude material was isolated by filtration, washed with water (234 kg) and dried under vacuum to constant weight. The crude material was dissolved in N,N-dimethylacetamide (252 kg) at 80° C. until all material had dissolved. The solution was cooled to 60° C. and heptane (918 kg) was slowly added over a period of 1 hour, maintaining a temperature above 35° C. The solution was cooled to 35° C. and stirred at 35° C. for a minimum of 1 hour. The solid was isolated by filtration, washed with heptane (250 kg) and dried to constant weight under vacuum. Yield: 92.5%; purity: 98.6%. The dry solid (83.1 kg) was added to a 1:1 mixture of ethanol and water (1V/1V; 1670 kg), and the mixture was heated to approximately 84° C. (reflux) until all material was in solution. The solution was cooled to 70° C. and polish-filtered, and then cooled to 30° C. over 2 hours. The solution was cooled to 0° C. The mixture was stirred at 0° C. for at least 1 hour, before the material was isolated by filtration, washed with ethanol/water (1V/1V; 33 kg) and dried under vacuum to constant weight. The material was passed through a 60-mesh screen to afford 2-(4-(2-hydroxyethoxy)-3,5-dimethylphenyl)-5,7-dimethoxyquinazolin-4(3H)-one (4). Yield: 66.4 kg; 79.9%.

Example 2

Compounds that can be Prepared Similar to Example 1

2-(4-(2-hydroxyethoxy)-3,5-dimethylphenyl)quinazolin-4(3H)-one;

2-(3-chloro-4-(2-hydroxyethoxy)phenyl)-5,7-dimethoxyquinazolin-4(3H)-one;

2-(4-(2-hydroxyethoxy)-3-methoxyphenyl)-5,7-dimethoxyquinazolin-4(3H)-one;

2-(4-(2-hydroxyethoxy)-3,5-dimethylphenyl)-6,7-dimethoxyquinazolin-4(3H)-one;

2-(4-(2-hydroxyethoxy)-3,5-dimethylphenyl)-5,7-dimethoxypyrido[2,3-d]pyrimidin-4(3H)-one;

N-(2-(4-(2-hydroxyethoxy)-3,5-dimethylphenyl)-4-oxo-3,4-dihydroquinazolin-6-yl)acetamide;

2-(4-(2-hydroxyethoxy)-3,5-dimethylphenyl)-5,7-dimethylquinazolin-4(3H)-one;

5,7-dichloro-2-(4-(2-hydroxyethoxy)-3,5-dimethylphenyl)quinazolin-4(3H)-one;

2-(4-(2-hydroxyethoxy)-3,5-dimethylphenyl)-6-methoxyquinazolin-4(3H)-one;

2-(4-(2-hydroxyethoxy)-3,5-dimethylphenyl)-5-methoxyquinazolin-4(3H)-one;

6-bromo-2-(4-(2-hydroxyethoxy)-3,5-dimethylphenyl)quinazolin-4(3H)-one; and 2-(4-(2-hydroxyethoxy)-3-methylphenyl)-5,7-dimethoxyquinazolin-4(3H)-one.

Example 3

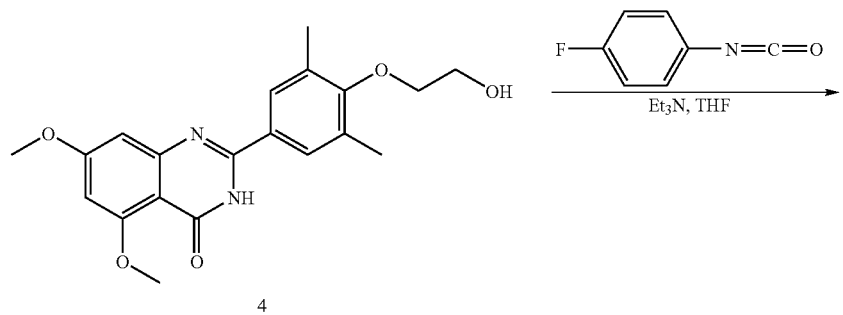

4

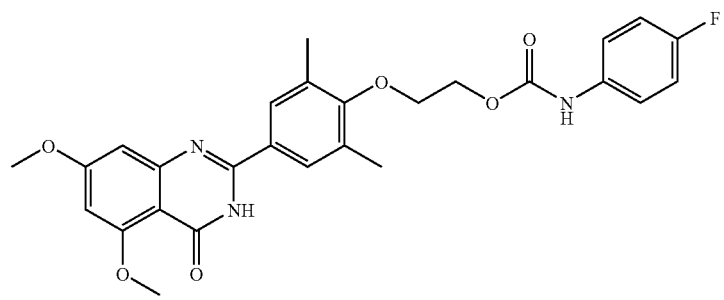

5

2-(4-(5,7-dimethoxy-4-oxo-3,4-dihydroquinazolin-2-yl)-2,6-dimethylphenoxy)ethyl 4-fluoro-phenylcarbamate (5)

A mixture of 4-fluorophenylisocyanate (0.138 mL, 1.14 mmol), Et$_3$N (0.185 mL, 1.32 mmol) and 4 (0.0700 g, 0.189 mmol) in THF (1.00 mL) was heated at reflux for 8 hours. The mixture was cooled, diluted with EtOAc (200 mL), washed with saturated aqueous NH$_4$Cl (3×75 mL), brine (75 mL), dried over Na$_2$SO$_4$, filtered and concentrated under vacuum. The residue was purified on silica gel (12 g, CH$_2$Cl$_2$/MeOH) and the product was freeze-dried from MeCN/H$_2$O to provide 2-(4-(5,7-dimethoxy-4-oxo-3,4-dihydroquinazolin-2-yl)-2,6-dimethylphenoxy)ethyl 4-fluoro-phenylcarbamate (5) (0.0710 g, 74%) as a white solid: $^1$H NMR (300 MHz, DMSO-d$_6$) δ 11.83 (s, 1H), 9.78 (s, 1H), 7.91 (s, 2H), 7.54-7.44 (m, 2H), 7.18-7.08 (m, 2H), 6.73 (d, J=2.31 Hz, 1H), 6.51 (d, J=2.31 Hz, 1H), 4.47-4.38 (m, 2H), 4.12-4.03 (m, 2H), 3.89 (s, 3H), 3.84 (s, 3H), 2.31 (s, 6H); MS (APCI) m/z 508 [C$_{27}$H$_{26}$FN$_3$O$_6$+H]$^+$.

Example 4

2-(4-(5,7-Dimethoxy-4-oxo-3,4-dihydroquinazolin-2-yl)-2,6-dimethylphenoxy)ethyl cyclohexylcarbamate can be prepared using a procedure similar to Example 3.

Example 5

2-(3,5-Dimethyl-4-(2-(methylamino)ethoxy)phenyl)-5,7-dimethoxy-quinazolin-4(3H)-one To a mixture of 4 (2.00 g, 5.40 mmol) and Et$_3$N (0.977 mL, 7.02 mmol) in CH$_2$Cl$_2$ (27.0 mL) was added slowly MsCl (0.543 mL, 7.02 mmol) at room temperature. After 1 day, additional Et$_3$N (0.977 mL, 7.02 mmol) and MsCl (0.543 mL, 7.02 mmol) was added and the mixture was stirred for 2 hours, then diluted with EtOAc (300 mL) and washed with 10% aqueous citric acid (3×75 mL), saturated aqueous NaHCO$_3$ (75 mL), and brine (75 mL). An insoluble white solid was collected by filtration to provide mesylate 6 (0.890 g, 37%): $^1$H NMR (300 MHz, DMSO-d$_6$) δ 11.84 (s, 1H), 7.91 (s, 2H), 6.74 (d, J=2.32 Hz, 1H), 6.52 (d, J=2.32 Hz, 1H), 4.59-4.48 (m, 2H), 4.15-4.04 (m, 2H), 3.89 (s, 3H), 3.84 (s, 3H), 3.25 (s, 3H), 2.32 (s, 6H).

The mesylate (6) (0.200 g, 0.446 mmol) and 33% CH$_3$NH$_2$ in EtOH (5.00 mL) was heated at reflux overnight. The solvent was removed under vacuum and the residue was purified on silica gel (12 g, CH$_2$Cl$_2$/CH$_3$OH) and the product freeze-dried from MeCN/H$_2$O to provide 2-(3,5-dimethyl-4-(2-(methylamino)ethoxy)phenyl)-5,7-dimethoxy-quinazolin-4(3H)-one (7) (0.0968 g, 57%) as a light yellow solid: $^1$H NMR (300 MHz, DMSO-d$_6$) δ 7.90 (s, 2H), 6.73 (d, J=2.29 Hz, 1H), 6.52 (d, J=2.29 Hz, 1H), 3.94-3.80 (m, 8H), 2.98 (t, J=5.46 Hz, 2H), 2.45 (s, 3H), 2.33-2.28 (m, 8H); MS (APCI) m/z 384 [C$_{21}$H$_{25}$N$_3$O$_4$+H]$^+$.

Example 6

2-(3,5-Dimethyl-4-(2-(methoxy)ethoxy)phenyl)-5,7-dimethoxy-quinazolin-4(3H)-one can be prepared using a procedure similar to Example 5, where the mesylate (6) is treated with NaOMe in MeOH or MeOH/K$_2$CO$_3$ instead of CH$_3$NH$_2$.

Example 7

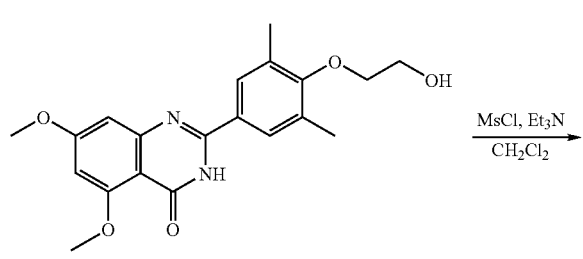

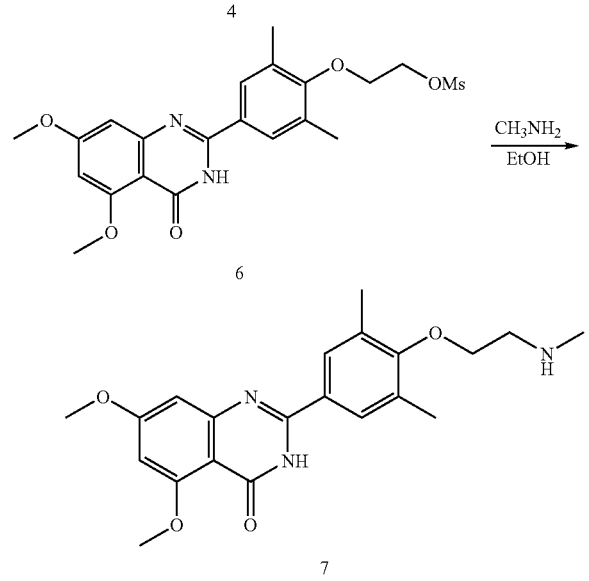

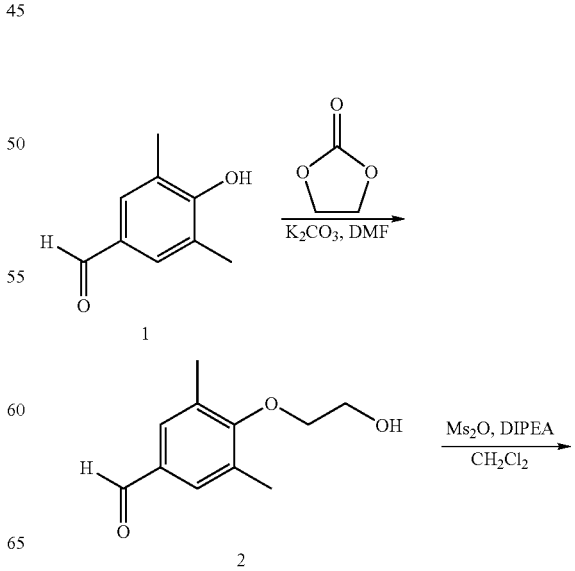

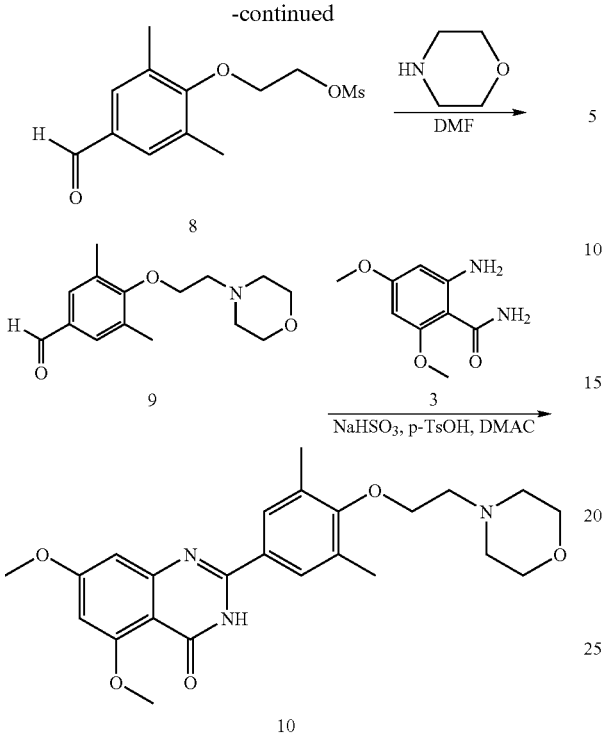

2-(3,5-Dimethyl-4-(2-(morpholino)ethoxy)phenyl)-
5,7-dimethoxy-quinazolin-4(3H)-one (10)

Intermediate 2 is obtained from 1 according to the procedure in Example 1. To a mixture of 2 and diisopropylethylamine in CH$_2$Cl$_2$ at 0° C. is added Ms$_2$O. The reaction mixture is stirred until the reaction is complete, as determined by thin layer chromatography (TLC). The reaction mixture is diluted with ethyl acetate and washed with cold sat. NaHCO$_3$ and brine. The organic layer is dried over Na$_2$SO$_4$, filtered and concentrated to provide mesylate 8.

A mixture of compound 8 and morpholine in DMF is heated to 50° C. The reaction mixture is stirred until the reaction is complete, as determined by TLC. The reaction mixture is cooled to room temperature and ethyl acetate is added. The mixture is washed with water, dried over Na$_2$SO$_4$, filtered and concentrated to provide crude intermediate 9. The crude product is purified by column chromatography to provide pure intermediate 9.

Starting material 3 and intermediate 9 are combined in DMAC followed by the addition of p-TsOH and sodium bisulfite. The reaction mixture is heated to 115° C. The reaction is stirred until complete as determined by TLC. The reaction mixture is cooled to room temperature and water is added. The mixture is extracted with CH$_2$Cl$_2$ three times. The combined organic layers are washed with water, dried over Na$_2$SO$_4$, filtered and concentrated. The crude product is purified by chromatography to provide 2-(3,5-dimethyl-4-(2-(methylamino)ethoxy)phenyl)-5,7-dimethoxy-quinazolin-4(3H)-one (10).

All references referred to herein are incorporated by reference in their entirety. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A method of preparing a compound of Formula I:

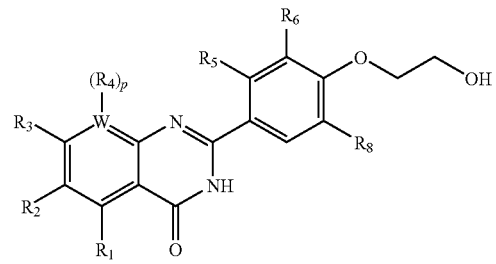

Formula I and solvates, hydrates, tautomers, and pharmaceutically acceptable salts thereof, wherein:
R$_1$, R$_2$, R$_3$, and R$_4$ are each independently selected from alkoxy, alkyl, amido, aryloxy, cycloalkyl, halogen, heterocyclyl, hydrogen, and nitro;
R$_6$ is selected from alkyl, alkoxy, and halogen;
R$_5$ is hydrogen, or R$_5$ and R$_6$ may be taken together with the carbon atoms to which they are attached, to form a ring selected from aryl, cycloalkyl, and heterocycyl;
R$_8$ is selected from alkyl, alkoxy, halogen, and hydrogen;
W is C and p is 1; comprising
a) reacting an aldehyde of Formula II:

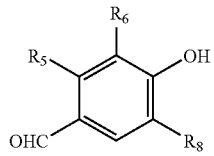

Formula II wherein R$_5$, R$_6$ and R$_8$ are as defined above, with ethylene carbonate to form a compound of Formula III:

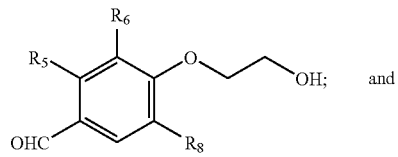

Formula III b) reacting the compound of Formula III with a compound of Formula IV

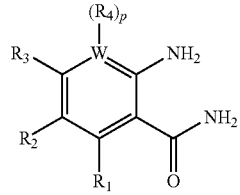

Formula IV wherein $R_1$, $R_2$, $R_3$, and $R_4$ are as defined above, to form the compound of Formula I.

2. The method according to claim 1, wherein $R_6$ and $R_8$ are each independently selected from alkyl and halogen.

3. The method according to claim 2, wherein $R_6$ and $R_8$ are each methyl.

4. The method according to claim 1, wherein $R_1$ and $R_3$ are each independently selected from alkoxy, alkyl, halogen, and hydrogen.

5. The method according to claim 4, wherein $R_1$ and $R_3$ are each methoxy.

6. The method according to claim 1, wherein the compound of Formula I is selected from:

2-(4-(2-hydroxyethoxy)-3,5-dimethylphenyl)quinazolin-4(3H)-one;

2-(3-chloro-4-(2-hydroxyethoxy)phenyl)-5,7-dimethoxyquinazolin-4(3H)-one;

2-(4-(2-hydroxyethoxy)-3-methoxyphenyl)-5,7-dimethoxyquinazolin-4(3H)-one;

2-(4-(2-hydroxyethoxy)-3,5-dimethylphenyl)-5,7-dimethoxyquinazolin-4(3H)-one;

2-(4-(2-hydroxyethoxy)-3,5-dimethylphenyl)-6,7-dimethoxyquinazolin-4(3H)-one;

N-(2-(4-(2-hydroxyethoxy)-3,5-dimethylphenyl)-4-oxo-3,4-dihydroquinazolin-6-yl)acetamide;

2-(4-(2-hydroxyethoxy)-3,5-dimethylphenyl)-5,7-dimethylquinazolin-4(3H)-one;

5,7-dichloro-2-(4-(2-hydroxyethoxy)-3,5-dimethylphenyl)quinazolin-4(3H)-one;

2-(4-(2-hydroxyethoxy)-3,5-dimethylphenyl)-6-methoxyquinazolin-4(3H)-one;

2-(4-(2-hydroxyethoxy)-3,5-dimethylphenyl)-5-methoxyquinazolin-4(3H)-one;

6-bromo-2-(4-(2-hydroxyethoxy)-3,5-dimethylphenyl)quinazolin-4(3H)-one; and 2-(4-(2-hydroxyethoxy)-3-methylphenyl)-5,7-dimethoxyquinazolin-4(3H)-one, and solvates, hydrates, tautomers, and pharmaceutically acceptable salts thereof.

7. The method according to claim 6, wherein the compound of Formula I is 2-(4-(2-hydroxyethoxy)-3,5-dimethylphenyl)-5,7-dimethoxyquinazolin-4(3H)-one, or a solvate, hydrate, tautomer, or pharmaceutically acceptable salt thereof.

* * * * *